United States Patent
Lang

(10) Patent No.: US 6,716,447 B1
(45) Date of Patent: *Apr. 6, 2004

(54) STABLE CAROTENE XANTHOPHYLL BEADLET COMPOSITIONS AND METHODS OF USE

(75) Inventor: John C. Lang, Cedar Hill, TX (US)

(73) Assignee: Alcon, Inc., Hunenberg (CH)

( * ) Notice: Subject to any disclaimer, the term of this patent is extended or adjusted under 35 U.S.C. 154(b) by 0 days.

This patent is subject to a terminal disclaimer.

(21) Appl. No.: 10/088,188

(22) PCT Filed: Sep. 6, 2000

(86) PCT No.: PCT/US00/24439

§ 371 (c)(1),
(2), (4) Date: Mar. 14, 2002

(87) PCT Pub. No.: WO01/19383

PCT Pub. Date: Mar. 22, 2001

(51) Int. Cl.⁷ .............................................. A61K 47/00
(52) U.S. Cl. ...................................................... 424/439
(58) Field of Search ......................................... 424/439

(56) References Cited

U.S. PATENT DOCUMENTS

| | | |
|---|---|---|
| 2,917,539 A | 12/1959 | Isler et al. |
| 3,998,753 A | 12/1976 | Antoshkiw et al. |
| 4,254,100 A | 3/1981 | Keller et al. |
| 4,522,743 A | 6/1985 | Horn et al. |
| 4,670,247 A | 6/1987 | Scialpi |
| 4,726,955 A | 2/1988 | Horn et al. |
| 5,308,759 A | 5/1994 | Gierhart |
| 5,350,773 A | 9/1994 | Schweikert et al. |
| 5,356,636 A | 10/1994 | Schenider et al. |
| 5,364,563 A | 11/1994 | Cathrein et al. |
| 5,382,714 A | 1/1995 | Khachik |
| 5,460,823 A | 10/1995 | Jensen et al. |
| 5,466,599 A | 11/1995 | Jacobson et al. |
| 5,492,701 A | 2/1996 | Cervos et al. |
| 5,500,415 A | 3/1996 | Dollar et al. |
| 5,527,533 A | 6/1996 | Tso et al. |
| 5,607,707 A | 3/1997 | Ford et al. |
| 5,648,564 A | 7/1997 | Ausich et al. |
| 5,668,183 A | 9/1997 | Leuenberger |
| 5,747,544 A | 5/1998 | Garnett et al. |
| 5,871,766 A | 2/1999 | Hennekens |
| 5,891,907 A | 4/1999 | Kolter et al. |
| 5,895,652 A | 4/1999 | Giampapa |
| 5,955,102 A | 9/1999 | Gorenbein et al. |

FOREIGN PATENT DOCUMENTS

| | | |
|---|---|---|
| WO | WO 98/11789 | 3/1998 |
| WO | WO 98/33494 | 8/1998 |

OTHER PUBLICATIONS

Berman, Biochemistry of the Eye, (Plenum, 1991).
Bernstein et al., Retinal Tubulin Binds Macular Carotenoids, Inv Ophthal & Vis Sci, vol. 38, No. 1, pp. 167–175 (1997).
Hammond et al., Cigarette smoking and retinal carotenoids: implications for age–related macular degeneration, Vision Research, vol. 36, pp. 3003–3009 (1996).
Hammond et al., Dietary modification of human macular pigment density, IOVS, vol. 38, pp. 1795–1801 (1997).
Hammond et al., Sex differences in macular pigment optical density: relation to plasma carotenoid concentrations and dietary patterns, Vision Research, vol. 36, pp. 2001–2012 (1996).
Handelman et al., Biological Control of Primate macular Pigment: Biochemical and Densitometric Studies, Inv Ophthal & Vis Sci, vol. 32, No. 2, pp. 257–267 (1991).
Seddon et al., Dietary Carotenoids, Vitamins A, C and E, and Advanced Age–Related macular Degeneration, JAMA, vol. 272, No. 8, pp. 1413–1420 (1994).
Snodderly, Evidence for protection against age–related macular degeneration by carotenoids and antioxidant vitamins, Am J Clin Nutr, vol. 62(suppl), pp. 1448S–1461S (1995).

*Primary Examiner*—Shelley A. Dodson
(74) *Attorney, Agent, or Firm*—Teresa J. Schultz

(57) ABSTRACT

Beadlets comprising xanthophylls and carotenes and/or retinoids, dietary supplements comprising these beadlets and methods of use are disclosed.

15 Claims, No Drawings

STABLE CAROTENE XANTHOPHYLL BEADLET COMPOSITIONS AND METHODS OF USE

This application is based on application Ser. No. 09/397,472, filed Sep. 17, 1999.

BACKGROUND OF THE INVENTION

Dietary supplements are taken for a variety of reasons including the improvement of vision or prophylaxis of vision loss. An example of a set of dietary supplements useful in promoting healthy eyes are the ICAPS® Dietary Supplements (Alcon Laboratories, Inc., Fort Worth, Tex.). Dietary supplements are generally in the form of powders, tablets, capsules or gel-caps and comprise a variety of vitamins, minerals, and herbal or other organic constituents. Some dietary supplements are formulated with beadlets.

Beadlets contain dietary substances and are generally small spheroids of less than about a millimeter in diameter. There are a variety of functions and purposes of beadlets. For example, beadlets may provide for the separate containment of ingredients within the dietary supplement to improve the stability of the entrapped ingredients.

Various beadlet compositions are known and can be obtained from a number of food ingredient or pharmaceutical manufacturers including H. Reisman Corp. (Orange, N.J.), BASF (Mount Olive, N.J.) and Hoffmann-LaRoche (Nutley, N.J.). Particular beadlet compositions have been the subject of several patents including U.S. Pat. Nos. 4,254,100 (Keller et al.) and 3,998,753 (Antoshkiw et al.). Methods of beadlet manufacture have been disclosed in U.S. Pat. Nos. 4,670,247 (Scialpi) and 3,998,753.

Current beadlet compositions used in dietary supplements generally are restricted to the use of inert ingredients and excipients complementary to a single nutritional compound. In other instances, when molecules of the same class are refined from a particular source, for example a major component with a minor related constituent, and both compounds produce parallel effects, such molecules may not necessarily be isolated but mixed together in a beadlet. These may be considered pseudo-single-component beadlets, and there are examples in the market place, e.g., Lutrinol® and FloraGLO® beadlets, which are a combination of lutein and zeaxanthin as formulated in Retoxil® Dietary Supplements. Examples of ingredients benefiting from beadlet confinement have included natural vitamins such as Vitamins A, D, E, and K; xanthophylls such as lutein, zeaxanthin, canthaxanthin, and astaxanthin; and carotenes, such as beta-carotene, lycopene, and retinol.

Recent data has suggested that the inclusion of xanthophylls and other carotenoids in dietary supplements may provide superior dietary supplements useful in enhancing the health of the eye. Studies have shown the selective uptake of the carotenoids, zeaxanthin and lutein, by the macula of the eye (Bernstein et al., *Retinal Tubulin Binds Macular Carotenoids*, Inv Ophthal & Vis Sci, volume 38, No. 1, pages 167–175 (1997); Hammond et al., *Dietary Modification of Human Macular Pigment Density*, Inv Ophthal & Vis Sci, volume 38, No. 9, pages 1795–1801 (1997); and Handelman et al., *Biological Control of Primate Macular Pigment: Biochemical and Densitometric Studies*, Inv Ophthal & Vis Sci, volume 32, No. 2, pages 257–267 (1991)).

Xanthophylls are effective phytochemical antioxidants and are known to localize in the macula of the retina. It has been suggested that the particular xanthophylls, zeaxanthin and its isomer lutein, may be beneficial in improving the health of the macula and the clarity of the lens. These molecules may function in a number of ways to protect the eye from high intensity radiation or other insults. It has been suggested that foveal proteins bind the xanthophylls and localize xanthophylls within the fovea. Since xanthophylls are capable of absorbing photoexcitative radiation of short visible wavelength, they also may shield the light-sensitive, underlying cells of the fovea. Such cells are responsible for high-definition vision and have been shown by epidemiological studies to be adversely affected by exposure to high intensity radiation or even chronic exposure to visible wavelength radiation. The carotenoids are believed to complement the activity of these cells, and also to protect them against photochemical insult. See, eg., Snodderly, *Evidence for protection against age-related macular degeneration by carotenoids and antioxidant vitamins*, Am J Clin Nutr, volume 62 (suppl), pages 1448S–1461S (1995) and Seddon et al., *Dietary Carotenoids, Vitamins A, C and E, and Advanced Age-Related Macular Degeneration*, JAMA, volume 272, No. 8, pages 1413–1420 (1994).

Studies have also shown that the portion of the retina associated with xanthophyll deposition undergoes one of the highest metabolic rates in the body (Berman, *Biochemistry of the Eye*, (Plenum, 1991). The energy to sustain this metabolism is derived from oxidation. While xanthophylls do not appear to undergo rapid turnover characteristic of water-soluble antioxidants (Hammond, et al., *Dietary modification of human macular pigment density*, IOVS, volume 38, pages 1795–1801 (1997)), continuous exchange of xanthophylls occurs in response to both environmental challenge and tissue environment, and their depletion without nutritional replacement may portend tissue damage (Hammond, et al., *Sex differences in macular pigment optical density: relation to plasma carotenoid concentrations and dietary patterns*, Vision Research, volume 36, pages 2001–2012 (1996); Hammond, et al., *Cigarette smoking and retinal carotenoids: implications for age-related macular degeneration*, Vision Research, volume 36, pages 3003∝3009 (1996); and Seddon, et al., *Dietary carotenoids, vitamins A, C, and E, and advanced age-related macular degeneration*, JAMA, volume 272, pages 1413–1420 (1994)).

The carotenes are conjugated $C_{40}$ compounds that include beta carotene (a provitamin A precursor). The carotenes are deeply colored compounds and are found throughout the plant kingdom, e.g., in leafy vegetables such as spinach and kale, and brilliantly colored fruits such as melons and pineapple. While the carotenes are ubiquitous in the plant kingdom, they generally are not available biosynthetically in mammals. Since the carotenes are essential for normal mammalian health, mammals need to ingest various sources of the carotenes, e.g., fruits and vegetables. In particular, the absence of carotenoids from the diet, especially the carotene derivative, vitamin A, is known to be associated with degenerative eye diseases.

SUMMARY OF THE INVENTION

The present invention is directed to improved beadlet formulations useful for inclusion in dietary supplements. In particular, the improved beadlets comprise one or more xanthophylls; one or more carotenes, retinoids or combinations thereof; one or more antioxidants; and excipients. Preferred beadlets may also contain one or more bioflavonoids. The beadlets are particularly useful for incorporation in dietary supplements customized for improving ocular nutrition.

The present invention is also directed to improved dietary supplements comprising the improved beadlets. Preferred dietary supplements have been formulated as an aid to ocular health. The present invention is also directed to methods of using the beadlets and dietary supplements for improving nutritional health. The methods of the present invention are particularly directed to the enhancement of ocular health and the prophylaxis of retinal disorders, including age-related macular degeneration.

One advantage of the beadlets of the present invention is that they provide one or more xanthophylls and one or more carotenes in a single beadlet formulation. Because these molecules contain multiple, conjugated double bonds, they are highly susceptible to degradation. Consequently, antioxidants have been required in dietary supplements to prevent premature oxidation of xanthophylls and carotenes during processing, manufacture, and storage. By coupling these mutually vulnerable components and the necessary antioxidants in one beadlet, the amount of stabilizing (antioxidant) component in the overall dietary supplement can be reduced, since the stabilizing components are distributed more proximately to the xanthophylls and carotenes, thereby concurrently stabilizing both of these carotenoids. In addition, the carotenes and xanthophylls, together in a single beadlet, may serve to stabilize each other. Since the stabilizing antioxidant components are often in excess of the active xanthophyll and carotene component, the total amount of the stabilizing antioxidant and other excipients including osmolality modifiers and polymers can become important, especially in a dosage form in which the presence of excess excipient diminishes the amount of the nutritional components that can be contained in the dosage form. In other words, an excess of excipient may displace crucial amounts of other vitamins, minerals or other dietary substances in the dosage form.

Another advantage of the beadlets of the present invention is that the juxtaposition of the carotenes and xanthophylls in a single beadlet, with or without absorption enhancing excipients, may allow for absorption synergy and/or activity synergy, leading to enhanced nutritional efficacy of the dietary supplement. Such synergy may arise, for example, when their properties—physical, chemical or physiological—are sufficiently similar that the bioavailability or site-specific targeting of these active ingredients may be manipulated concurrently using the single beadlet technology.

A related advantage of the coupling of these and other nutritional components into one beadlet is the potential for manipulating and improving competitive absorption of these agents. For example, if the beadlets are also comprised of a timed-release polymer, the release of the nutritional components may be controlled and thus synchronized, e.g., delivering them to the upper intestine at the same time where solubilization by chylomicra forming bile salts can facilitate synchronous absorption.

Another advantage of the beadlets is that, as a practical matter of formulation, the amounts of xanthophyll and carotene can be manipulated better as a single beadlet entity, as opposed to adjusting the individual xanthophyll and carotene components of the finished dietary supplement. In other words, the beadlet composition may be significantly altered while the dietary supplement preparation using the same size and number of beadlets (but now different beadlet composition) would be unaffected. For example, little or no change in dietary supplement preparation would be expected for a change in formulations in which a 3% lutein/0% zeaxanthin/3% weight/weight ("w/w") Vitamin A containing beadlet was replaced by a 0% lutein/3% zeaxanthin/3% w/w Vitamin A containing beadlet. And in both cases the amount of both the complementary antioxidant and other supplementary constituents within the beadlet may remain invariant. This simplifies the reformulation process of a complex dietary supplement (often containing 30 or more components) and would be useful in view of the need to respond to new scientific information directing modifications of nutritional components of dietary supplements. This advantage greatly improves the turn-around time and reduces the cost of reformulation of such dietary supplements.

Still another advantage of the beadlets of the present invention is that they allow better manipulation of the appearance of the dietary supplement. Because many carotenes and xanthophylls have multiple, conjugated double bonds, they are intensely colored (oranges to red) and hydrophobic. Thus, specialized techniques have been generally required to compress tablets containing such components so that the dietary supplement form does not crumble and the components do not "bleed" within the supplement form, and to coat the beadlet-containing supplement form uniformly and consistently so that no unattractive discoloration or pitting occurs. Combining the carotenes and xanthophylls in a single beadlet lessens the problems of tableting and tablet coating. Thus, once having developed a dietary supplement using a coating technology capable of screening and disguising imperfections introduced by the beadlet onto the surface of the dosage form, minor reformulations of a single complex beadlet, would obviate the requirement to redevelop the entire dietary supplement coating and tableting technologies.

The application of the beadlet technology of the present invention to dietary supplements provides, and facilitates development of, enhanced nutritional supplementation. Such technology may aid in increasing bioavailability of the dietary substances and also provide ease in modifying compositions containing xanthophylls/carotenes and complementary antioxidants within the supplement. Such improvements are believed to be particularly useful in the enhancement of ocular nutrition and improved ocular health.

DETAILED DESCRIPTION OF THE INVENTION

The present invention is directed to improved beadlet formulations, improved dietary supplement formulations comprising the improved beadlets and methods of use. As used herein, "dietary supplement(s)" or the shortened form, "supplement(s)," refer to any finished, dietary supplement dosage form containing dietary substances and suitable for ingestion by a host, e.g., human or other mammal.

The beadlets of the present invention comprise one or more xanthophylls; one or more carotenes or retinoids or combinations thereof; one or more antioxidants; and one or more solidifying agents.

As used herein, "xanthophylls" refer to hydroxy- and keto-oxidized carotenes and their derivatives; "carotenes" refer to any of the 40-carbon carotenes and their derivatives; "retinoids" refers to the 20-carbon Vitamin A (retinol) and its derivatives; and "carotenoids" refers to any of the xanthophylls, carotenes and retinoids or combinations thereof. Carotenoids may be synthetically derived or purified from natural sources. Synthetic preparations may contain different isomers of carotenoids than those contained in the natural preparations. Depending on intended use, natural, synthetic or mixtures of both types of carotenoids may be included in the beadlets of the present invention.

The xanthophyll component may be obtained from various sources such as vegetables and herbal components, such as corn, leafy green vegetables and marigolds; marine sources, such as krill; or microorganic sources, such as algae and gene-engineered bacterial or yeast sources. Xanthophylls may also be synthesized by methods known in the art and are available from various manufacturers. Examples of xanthophylls include, but are not limited to, lutein, zeaxanthin, astaxanthin, canthaxanthin, cryptoxanthin and related oleoresins (e.g., fatty acid mono and di-esters of xanthophylls). The xanthophyll purity and concentration in the various commercial sources will vary. For example, some sources may provide about a 1% weight/weight ("w/w") or less of xanthophyll in oil while other sources, e.g., Kemin Laboratories, Inc. (Des Moines, Iowa), may provide a source in excess of 20% w/w xanthophyll in oil. Xanthophyll sources may be preparations of individual xanthophylls or combinations thereof. For example, a xanthophyll preparation may comprise lutein as the sole xanthophyll or a combination of lutein and zeaxanthin. The inclusion of a combination of xanthophylls in the beadlets, and in particular ratios, may be particularly important when it is the intention to deliver such combinations to the host in ratios similar to those found in the retina broadly, or in the macula or fovea of the eye, specifically, or in other ratios which, when injested, support the ratios in the host tissues. Xanthophylls may also included in the beadlets as conjugated derivatives, e.g., oleoresins of xanthophylls, as exemplified above.

The carotene, retinoid or combinations thereof component (hereinafter referred to as "carotene(s)/retinoid(s)") may be obtained from various sources such as vegetable and herbal sources, such as corn and leafy vegetables, and fermentation product sources available from the biotech industry. The carotenes/retinoids may also be synthesized by methods known in the art. Examples of carotenes include, but are not limited to, alpha-, beta-, gamma-, delta-, epsilon- and psi-carotene, isomers thereof. Examples or retinoids include, but are not limited to, Vitamin A and Vitamin A analogs (e.g., retinoic acid). The carotene/retinoid purity and concentration in the various commercial sources will vary. For example, some sources may provide about a 1% w/w or less of carotene/retinoid in oil, or as an oil suspension, or in a protected dry form, e.g., a beadlet.

The concentrations of the xanthophylls and carotenes/retinoids in the beadlets will vary, but will be in amounts useful for inclusion of the beadlets in dietary supplements. In general, the combined concentration of xanthophylls and carotenes/retinoids in the beadlets will be in the range of about 0.1 to 10% w/w. Preferred carotenoid concentrations, which are generally dependent on the selection of particular carotenes/retinoids and xanthophylls and their relative ratios, will be about 0.5 to 7% w/w. The individual concentrations of the xanthophylls and the carotenes/retinoids will not necessarily be the same. Preferred beadlets will have a concentration ratio from about 1:10 to about 10:1 of xanthophylls:carotenes/retinoids and the most preferred beadlets will have concentration ratios from about 2:1 to about 1:2 of xanthophylls:carotenes/retinoids.

The most preferred beadlets of the present invention will comprise 0.5 to 7% w/w of lutein/zeaxanthin (xanthophylls) and 0.5 to 7% w/w of β-carotene (carotenes/retinoids).

As stated above, the beadlets will also contain one or more antioxidants. The antioxidants can be hydrophobic or hydrophilic. The antioxidants serve to inhibit the oxidative, photochemical and/or thermal degradation of the carotenoid components. Since antioxidants are also thought to be useful in nutritional health, they may also provide some nutritional benefit to the host. In general, the antioxidants will be natural antioxidants or agents derived therefrom. Examples of natural antioxidants and related derivatives include, but are not limited to, vitamin E and related derivatives, such as tocotrienols, alpha-, beta-, gamma-, delta- and epsilon-tocopherol, and their derivatives, such as the corresponding acetates, succinates; Vitamin C and related derivatives, e.g., ascorbyl palmitate; and natural oils, such as oil of rosemary. Preferred beadlets will contain one or more hydrophobic antioxidants. The amount of antioxidant(s) contained in the beadlet will be an amount effective to inhibit or reduce the oxidative, photochemical and/or thermal degradation of the carotenoid components. Such an amount is referred herein as "an effective amount of one or more antioxidants." In general, such an amount will range from about 0.1 to 10 times the amount of the xanthophyll and carotene/retinoid components and any other chemically sensitive components present, e.g., bioflavonoids. Preferred beadlets, which will generally comprise about 0.5–7% w/w of carotenoids alone, or including bioflavonoids, will contain about 2 to 10% w/w of antioxidant. The most preferred beadlets will contain Vitamin E and, optionally, ascorbyl palmitate.

The beadlets will also comprise one or more solidifying, bulking and agglomerating agents (collectively referred to herein as "solidifying agent(s)"). The solidifying agent(s) aid in transforming the carotenoid and antioxidant components into a solid suitable for granulation, tableting or blending prior to encapsulation, of the beadlet in the dietary supplement. The solidifying agents are particularly useful when the carotenoid/antioxidant components are in oils or oil suspensions. Examples of solidifying agents useful in the preparation of the beadlets include, but are not limited to, sucrose, glucose, fructose, starches (e.g., corn starch), syrups (e.g., corn syrup), and ionic and nonionic polymers including, but not limited to, PEGs and other poly ether-like alkoxy cellulosics (HPMC), gellan, carrageenans, *Eucheuma gelatenae*, hyaluronates, chondroitin sulfate, pectins, and proteins, (e.g., collagen or their hydrolyzed products (e.g., gelatins or polypeptides)). Other solidifying agents known to those skilled in the art of beadlet and dietary supplement preparation may also be used in the preparation of the beadlets of the present invention. The amount of solidifying agent(s) will vary, depending on the other components contained in the beadlet, but will generally comprise the majority weight and volume of the beadlet.

Optionally, the beadlets of the present invention may also contain one or more bioflavonoids and/or glycosidic bioflavonoids. Bioflavonoids, or "flavonoids," are flavone- and isoflavone-like structures found primarily in fruits and vegetables. Bioflavonoids are commercially available or may be synthesized by methods known in the art. Examples of bioflavonoids include, but are not limited to, quercetin, acacetin, liquritin, rutin, taxifulin, nobiletin, tangeretin, apigenin, chyrsin and kaempferol, and their derivatives, such as the corresponding methoxy-substituted analogs. The bioflavonoids may be useful in nutritional health as modulators of the rates of in vivo enzyme-mediated reactions. The bioflavonoids may also provide antioxidant activity and may be included in the beadlet for this purpose.

Other oils may be present in the beadlets of the present invention. The beadlets will typically comprise an amount of vegetable oils or oleoresins, since the separate carotene/retinoid and/or xanthophyll components to be added to the beadlets are generally commercially available as a diluted vegetable oil or oil suspension, or as an oleoresin extract. Such an amount of oil/oleoresin typically ranges from about 1 to 100 times the xanthophyll or carotene content in the beadlet. For example, a xanthophyll extract to be included in a beadlet may contain 20% w/w lutein, 2% w/w zeaxanthin and 78% vegetable oil/oleoresin. Other oils may also be included in the beadlets.

The beadlets of the present invention may also comprise additional excipients useful in preparing and finishing the beadlets. Such excipients may include timed-release polymer coating agents useful in prolonging dissolution of the beadlet in the digestive tract. Examples of such polymers include, but are not limited to ionic and nonionic polymers, such as PEGs and other poly ether-like alkoxy cellulosics (HPMC), gellan, carrageenans, *Eucheuma gelatenae*, starch, hyaluronates, chondroitin sulfate, pectins, and proteins, e.g., collagen. Since the xanthophyll/carotenes are highly pigmented, coating technology may be applied to the beadlet in order to provide a beadlet of uniform color. Examples of color coating agents may include, but are not limited to, polymers, colorants, sealants and surface active agents including, not limited to, fatty acids and esters, di- and triglycerides, phospholipids including mono- and di-alkyl glyceryl phosphates, nonionic agents (sugars, polysaccharides, e.g., HPMC and polysorbate 80) and ionic agents.

The above-described ingredients contained in the beadlets may, in some cases, form microspheres within the beadlet. The beadlets may be of various size and shape. In general, however, the beadlets will be spheroid with an approximate diameter of about 0.2 microns to 800 microns.

The beadlets may be manufactured using a number of techniques known in the art. For example, the beadlets may be prepared by blending and granulation of the ingredients, followed by drying. The details of these processes may vary according to the sequence of addition, duration and conditions for granulation, and techniques employed for drying. Preferred methods will include a low-temperature, low light-exposure drying step capable of maintaining stability of the beadlet. An inert, or reduced-oxygen, atmosphere may also be employed in the manufacture of the beadlets in order to further reduce degradation of sensitive components.

The following Examples 1–6 illustrate preferred beadlets of the present invention. The amount of water present in the following beadlet examples may vary due to process and storage conditions but will generally range from about 1–10% w/w; as such, the other component percentage amounts may fluctuate slightly, but will be in the same relative proportion with respect to each other.

EXAMPLE 1

| Ingredient | Amount (% w/w) |
| --- | --- |
| Beta Carotene (natural) | 3 |
| Lutein/zeaxanthin (natural) | 3 |
| Hydrolyzed Gelatin | 30 |
| Vegetable Oil/Oleoresin | 23 |
| Sucrose | 14.6 |
| Food Grade Corn Starch | 17 |
| Ascorbyl Palmitate | 2.7 |
| Tocopherol(s) | 1.7 |
| Water | 5 |

EXAMPLE 2

| Ingredient | Amount (% w/w) |
| --- | --- |
| Beta Carotene (natural) | 3 |
| Lutein | 2.7 |
| Zeaxanthin | 0.3 |

EXAMPLE 2-continued

| Ingredient | Amount (% w/w) |
| --- | --- |
| Hydrolyzed Gelatin | 30 |
| Vegetable Oil/Oleoresin | 23 |
| Sucrose | 14.6 |
| Food Grade Corn Starch | 17 |
| Ascorbyl Palmitate | 2.7 |
| Tocopherol(s) | 1.7 |
| Water | 5 |

EXAMPLE 3

| Ingredient | Amount (% w/w) |
| --- | --- |
| Beta Carotene (natural) | 3 |
| Lutein | 1.5 |
| Zeaxanthin | 1.5 |
| Hydrolyzed Gelatin | 30 |
| Vegetable Oil/Oleoresin | 23 |
| Sucrose | 14.6 |
| Food Grade Corn Starch | 17 |
| Ascorbyl Palmitate | 2.7 |
| Tocopherol(s) | 1.7 |
| Water | 5 |

EXAMPLE 4

| Ingredient | Amount (% w/w) |
| --- | --- |
| Beta Carotene (natural) | 3 |
| Lutein | 1.0 |
| Zeaxanthin | 1.0 |
| Astaxanthin | 1.0 |
| Hydrolyzed Gelatin | 30 |
| Vegetable Oil/Oleoresin | 23 |
| Sucrose | 14.6 |
| Food Grade Corn Starch | 17 |
| Ascorbyl Palmitate | 2.7 |
| Tocopherol(s) | 1.7 |
| Water | 5 |

EXAMPLE 5

| Ingredient | Amount (% w/w) |
| --- | --- |
| Beta Carotene (natural) | 2 |
| Lutein | 1.0 |
| Zeaxanthin | 1.0 |
| Astaxanthin | 1.0 |
| Quercetin | 1.0 |
| Hydrolyzed Gelatin | 30 |
| Vegetable Oil/Oleoresin | 23 |
| Sucrose | 14.6 |
| Food Grade Corn Starch | 17 |
| Ascorbyl Palmitate | 2.7 |
| Tocopherol(s) | 1.7 |
| Water | 5 |

EXAMPLE 6

| Ingredient | Amount (% w/w) |
| --- | --- |
| Beta Carotene (natural) | 1 |
| Lutein/zeaxanthin | 5 |
| Hydrolyzed Gelatin | 31.6 |
| Vegetable Oil/Oleoresin | 24 |
| Sucrose | 18 |
| Food Grade Corn Starch | 16 |

EXAMPLE 6-continued

| Ingredient | Amount (% w/w) |
|---|---|
| Ascorbyl Palmitate | 2.7 |
| Tocopherol(s) | 1.7 |

As stated above, the beadlets of the present invention may be incorporated in various dietary supplements. The dietary supplements of the present invention may be formulated as powders, two-piece hard shell capsules, gel-caps, tablets, or any other solid or semi-sold form that can be taken orally. The dietary supplements will generally comprise other vitamins, minerals and excipients. The amount of beadlets incorporated in the dietary supplements will vary, depending on various factors, such as total weight or volume of the dietary supplement form, the specific nutritional health objective, the presence of other components in the supplement, and so on. In general, however, the beadlets will be incorporated in the dietary supplements in an amount of from about 1 to 50% w/w of dietary supplement. Preferred dietary supplements will comprise the present invention beadlets in an amount of from 2 to 15% w/w of dietary supplement.

The types and amounts of the vitamins and minerals contained in the supplement, other than those contained in the beadlets, will depend on the type of supplement being prepared, i.e., the intended area of health to be treated/enhanced by the supplement and the dosing regimen.

The dietary supplements may also contain herbal or plant preparations or extracts. Examples of herbal or plant preparations or extracts useful in the dietary supplements include, but are not limited to, extracts from teas, fruits and vegetables (e.g., citrus fruits); dried, chopped or powdered leaves or films from vegetable products (e.g., berries, spinach, kale); extruded oils and oil soluble nutrients (e.g., grape seed extract); and hydrolyzed or natural protein, peptide and amino acid components.

Preferred dietary supplements comprising the beadlets of the present invention are intended to aid in ocular health. Various vitamins and minerals, in addition to the beadlets, may be added to such supplements, but in general, the supplements will contain Vitamin B-2 in an amount of about 0.5 to 40 milligrams ("mg")/tablet; Vitamin C in an amount of about 15 to 500 mg/tablet; Vitamin E in an amount of about 4 to 300 IU/tablet; copper in an amount of about 0.75 to 6 mg/tablet; manganese in an amount of about 0 to 10 mg/tablet; selenium in an amount of about 10 to 80 micrograms ("mcg")/tablet; and zinc (e.g., as zinc acetate) in an amount of about 7.5 to 80 mg/tablet. These quantities correspond to conventional tablets or capsules ranging in weight from about 200 mg to 1.5 grams.

Excipients useful in the dietary supplements include viscosity agents, emulsifiers, binding agents, buffers, bulking agents, coloring agents and water soluble coatings. Such excipients are well known in the art for preparing dietary supplements. Preferred excipients for inclusion in ocular-type dietary supplements include salts and acids (e.g., dicalcium phosphate, ascorbyl palmitate, calcium carbonate, calcium silicate, croscarmellose sodium, magnesium stearate, sodium ascorbate, sodium benzoate, sorbic acid), polymers and saccharides (e.g., HPMC, microcrystalline cellulose ("MCC")), gelatin, polyethylene glycol, starch, and sucrose), surface active agents and oils or waxes (e.g., magnesium stearate, lecithins, phospholipids, tocopherols, vegetable oils and oleoresin, carnauba wax), inert solids and colorants (e.g., silicon dioxide, titanium dioxide), and coating materials (e.g., the Opadry® coating materials).

The following Examples 7–12 are examples of preferred dietary supplements. Although the nutritional components and amounts are listed separately, such components are often added to the dietary supplement preparation as mixtures of the component along with ancillary excipients. For example, in Example 7, copper is actually added as 20 mg of a 10% w/w copper-amino acid chelate, yielding a final amount of 2.0 mg of copper. The chelate counter-ion is considered, for this accounting, an "ancillary excipient" as are other such unspecified inactive components/excipients. Specific, identifiable excipients added to the preparation, are listed separately.

EXAMPLE 7

A preferred dietary supplement tablet of the present invention, incorporating the beadlets of Example 1:

| Ingredient | Amount |
|---|---|
| Beadlet of Example 1 | 83 mg |
| Other nutrients: | |
| Vitamin B-2 | 6.5 mg |
| Vitamin C | 200 mg |
| Vitamin E | 75 IU |
| Copper | 2 mg |
| Manganese | 5 mg |
| Selenium | 20 mcg |
| Zinc (acetate) | 30 mg |
| Excipients: | |
| Dicalcium phosphate | 108 mg |
| HPMC (hydroxypropylmethylcellulose) | 93 mg |
| MCC (microcrystalline cellulose) | 46.5 mg |
| Magnesium stearate | 31 mg |
| Silicon dioxide | 34.5 mg |
| Sucrose | 0.9 mg |
| Polyethylene glycol | 2.7 mg |
| Gelatin | 67.7 mg |
| Polysorbate 80 | 0.2 mg |
| Sodium benzoate | 0.15 mg |
| Sorbic acid | 0.3 mg |
| Titanium dioxide | 7 mg |
| Carnauba wax | 0.04 mg |
| Ancillary excipients | 121 mg |

EXAMPLE 8

A preferred dietary supplement tablet of the present invention, incorporating any of the beadlets of Example 2–6, or combinations thereof:

| Ingredient | Amount |
|---|---|
| Beadlets | 83 mg |
| Other nutrients: | |
| Vitamin B-2 | 6.5 mg |
| Vitamin C | 200 mg |
| Vitamin E | 75 IU |
| Copper | 2 mg |
| Manganese | 5 mg |
| Selenium | 20 μg |
| Zinc (acetate) | 30 mg |
| Excipients: | |
| Dicalcium phosphate | 108 mg |
| HPMC (hydroxypropylmethylcellulose) | 93 mg |
| MCC (microcrystalline cellulose) | 46.5 mg |
| Magnesium stearate | 31 mg |
| Silicon dioxide | 34.5 mg |
| Sucrose | 0.9 mg |
| Polyethylene glycol | 2.7 mg |

-continued

| Ingredient | Amount |
| --- | --- |
| Gellatin | 67.7 mg |
| Polysorbate 80 | 0.2 mg |
| Sodium benzoate | 0.15 mg |
| Sorbic acid | 0.3 mg |
| Titanium dioxide | 7 mg |
| Carnauba wax | 0.04 mg |
| Ancillary excipients | 121 mg |

EXAMPLE 9

A preferred dietary supplement tablet of the present invention incorporating any of the beadlets of Example 1–6, or mixtures thereof:

| Ingredient | Amount |
| --- | --- |
| Beadlets | 80–120 mg |
| Other nutrients: | |
| Vitamin B-2 | 2 mg |
| Vitamin C | 65 mg |
| Vitamin E | 15 IU |
| Copper | 1 mg |
| Manganese | 3.5 mg |
| 1-Selenomethionine | 50 µg |
| Zinc (acetate) | 10 mg |
| Excipients: | |
| Calcium carbonate | 106 mg |
| MCC (microcrystalline cellulose) | 87 mg |
| Magnesium stearate | 6 mg |
| Silicon dioxide | 9 mg |
| HPMC | 15.3 mg |
| Calcium silicate | 1.4 mg |
| Starch | 11.7 mg |
| Titanium dioxide | 5 mg |
| Croscarmellose sodium | 6 mg |
| Polysorbate 80 | 0.2 mg |
| Dicalcium phosphate | 4 mg |
| Fish gelatin | 3.7 mg |
| Polyethylene glycol | 2.5 mg |
| Carnauba wax | 0.018 mg |
| Ancillary excipients | 47.3 mg |

EXAMPLE 10

A preferred dietary supplement gelatin capsule of the present invention incorporating any of the beadlets of Example 1–6, or mixtures thereof:

| Ingredient | Amount |
| --- | --- |
| Beadlets | 80–120 mg |
| Other nutrients: | |
| Thiamin (Vitamin B-1) | 1.4 mg |
| Riboflavin (Vitamin B-2) | 1.6 mg |
| Pyridoxine (Vitamin B-6) | 2 mg |
| Cyanocobalamin | 0.001 mg |
| Niacin | 18 mg |
| Ascorbic Acid | 60 mg |
| Vitamin E (d-alpha-tocopherol succinate) | 9 IU |
| Copper (as copper gluconate) | 0.5 mg |
| Zinc (as zinc acetate) | 5 mg |
| Manganese (as citrate) | 1 mg |
| Folate | 0.2 mg |
| Biotin | 0.15 mg |

-continued

| Ingredient | Amount |
| --- | --- |
| Pantothenic Acid | 6 mg |
| Selenium | 0.07 mg |
| Bilberry Herb Powder | 40 mg |
| Citrus Bioflavnoid Complex Powder | 250 mg |
| Grape Seed Extract with Leucoanthocyanins | 10 mg |
| Taurine | 50 mg |
| Polyphenol Catechins of Green Tea Extract | 50 mg |
| Spinach Leaf Powder | 50 mg |
| n-Acetyl 1-Cysteine (Anhydrous) | 50 mg |
| Excipients: | |
| Vegetable Derived Magnesium Stearate | 13 mg |
| Fine Silica Powder | 10 mg |
| Croscarmellose Sodium | 20 mg |
| White Opaque Gelatin Capsule | 115 mg |
| Ancillary Excipients | 0–100 mg |

EXAMPLE 11

A preferred dietary supplement gelatin capsule of the present invention incorporating any of the beadlets of Example 1–6, or mixtures thereof:

| Ingredient | Amount |
| --- | --- |
| Beadlets | 80–120 mg |
| Other nutrients: | |
| Thiamin (Vitamin B-1) | 0.8 mg |
| Riboflavin (Vitamin B-2) | 1.1 mg |
| Pyridoxine (Vitamin B-6) | 1.2 mg |
| Cyanocobalamin | 0.001 mg |
| Niacin | 16 mg |
| Ascorbic Acid | 60 mg |
| Vitamin E (d-alpha-tocopherol succinate) | 9 IU |
| Folate | 0.025 mg |
| Biotin | 0.3 mg |
| Pantothenic Acid | 4 mg |
| Selenium | 0.05 mg |
| Excipients: | |
| Vegetable Derived Magnesium Stearate | 10 mg |
| Fine Silica Powder | 8 mg |
| Croscarmellose Sodium | 12 mg |
| White Opaque Gelatin Capsule | 95 mg |
| Ancillary Excipients | 0–100 mg |

EXAMPLE 12

A preferred dietary supplement gelatin capsule of the present invention, incorporating any of the beadlets of Example 1–6, or mixtures thereof:

| Ingredient | Amount |
| --- | --- |
| Beadlets | 25–100 mg |
| Other nutrients: | |
| Vitamin C | 80 mg |
| Vitamin E | 70 IU |
| Vitamin B-1 | 1 mg |
| Vitamin B-2 | 1.133 mg |
| Niacin | 13.33 mg |
| Vitamin B-6 | 2 mg |
| Folate | 133.33 mcg |
| Vitamin B-12 | 10 mcg |

-continued

| Ingredient | Amount |
|---|---|
| Biotin | 50 mcg |
| Pantothenic Acid | 6.67 mg |
| Vitamin D | 26.67 mg |
| Selenium | 33.33 mcg |
| Zinc | 5 mg |
| Copper | 0.67 mg |
| Manganese | 0.67 mg |
| Chromium | 33.33 mcg |
| Magnesium | 16.67 mg |
| Calcium | 33.33 mg |
| Potassium | 33 mg |
| Citrus Bioflavonoids | 133.33 mg |
| Polyphenol Catechins | 33.33 mg |
| Spinach Leaf Powder | 16.67 mg |
| Bilberry Herb | 20 mg |
| Blueberry Fruit Powder | 10 mg |
| Leucoanthocyanins | 3.33 mg |
| n-acetyl 1-cysteine | 16.67 mg |
| Glutathione | 5 mg |
| Alpha Lipoic Acid | 3.33 mg |
| Excipients: | |
| Vegetable Derived Magnesium Stearate | 13 mg |
| Fine Silica Powder | 10 mg |
| Croscarmellose Sodium | 20 mg |
| White Opaque Gelatin Capsule | 115 mg |
| Ancillary Excipients | 0–100 mg |

The dietary supplements of the present invention may be used to treat various disorders and to enhance the health of particular tissues and the overall health of the patient.

Preferably, the dietary supplements of the present invention will be used to treat ocular diseases and disorders and to improve the ocular health of the patient. The methods of the present invention are particularly directed to the administration of the dietary supplements for improving the ocular health of patients under treatment for glaucoma, and other diseases and disorders of the retina and its support tissues, particularly age related macular degeneration, retinal ischemia, acute retinopathies associated with trauma, post-surgical complications, the damage associated with laser therapy including photodynamic therapy (PDT), and surgical light induced iatrogenic retinopathy. As used herein, "retina or optic nerve head neuropathy" refers to any of the foregoing diseases or other retinal or optic nerve head neurodegenerative diseases.

The use of the dietary supplements of the present invention to prevent, treat or ameliorate macular degeneration is a particularly preferred embodiment of the methods of the present invention. As sated in the Background of the Invention, there is some indication that certain xanthophylls, e.g., lutein and zeaxathin, may be useful/necessary in the prevention/treatment/amelioration of macular degeneration. The present invention dietary supplements contain xanthophylls and carotenes and/or retinoids together in beadleted form is such that such supplement compositions are believed to provide improved nutrition of the macula and, hence, improved methods of preventing, treating or ameliorating macular degeneration.

Dosing regimens will vary, depending on the particular dietary supplement components and amounts, and the age, weight, sex, diet and ancillary medication taken by the patient and severity of the condition to be treated (or prophylaxis to be obtained). Dosing regimens will also depend on the form of the dietary supplement and the potency of the dietary supplement to be taken. Such determinations may be assessed by clinicians skilled in the art but, in general, 1–4 dietary supplements will be taken per day.

I claim:

1. A beadlet comprising two or more carotenoids; an antioxidant in an amount effective to inhibit the degradation of the carotenoid components; and one or more solidifying agents; wherein said carotenoids comprise one or more xanthophylls and one or more carotene/retinoids; wherein the total amount of xanthophyll is from about 0.1% to 10% w/w and the total amount of carotene/retionoid is from about 0.1% to 10% w/w.

2. The beadlet of claim 1, wherein the amount of antioxidant is from about 0.1 to 10 times the total amount of the carotenoid components.

3. The beadlet of claim 2, wherein the total amount of carotenoid components is from about 0.5% to 7% w/w and the amount of antioxidant is from about 2% to 10% w/w.

4. The beadlet of claim 1, further comprising a bioflavonoid, wherein the total amount of carotenoid components and bioflavanoid is from about 0.5% to 7% w/w.

5. A beadlet comprising a xanthophyll extract; one or more carotene/retinoid selected from the group consisting of alpha-carotene, beta-carotene, gamma-carotene, delta-carotene, epsilon-carotene, psi-carotene, Vitamin A and Vitamin A analogs; a natural antioxidant selected from the group consisting of Vitamin E, tocotrienols, alpha-tocopherol, beta-tocopherol, gamma-tocopherol, delta-tocopherol, epsilon-tocopherol, Vitamin C, ascorbyl palmitate, and natural oils; and a solidifying agent, said xanthophyll comprising lutein, zeaxanthin and vegetable oil/oleoresin, and wherein said beadlet is from 0.2 microns to 800 microns in diameter.

6. The beadlet of claim 5, wherein said xanthophyll extract comprises 20% lutein, 2% zeaxanthin and 78% vegetable oil/oleoresin, said carotene/retinoid is beta-carotene, and said antioxidant is oil of rosemary; and wherein the total amount of xanthophyll is from about 0.5% to 7% w/w, the total amount of beta-carotene is from 0.5% to 7% w/w and the total amount of oil of rosemary is from 2% to 10% w/w, said beadlet further comprising coating.

7. The beadlet of claim 6, wherein the ratio of lutein and zeaxanthin to beta-carotene is from about 2:1 to about 1:2.

8. A dietary supplement comprising the beadlet of claim 5.

9. A dietary supplement comprising the beadlet of claim 6.

10. A dietary supplement comprising the beadlet of claim 7.

11. The dietary supplement of claim 10, further comprising Vitamin C, Vitamin E, copper and zinc.

12. A method of improving ocular health comprising administering to a mammal the dietary supplement of claim 8.

13. A method of improving ocular health comprising administering to a mammal the dietary supplement of claim 9.

14. A method of improving ocular health comprising administering to a mammal the dietary supplement of claim 10.

15. A method of improving ocular health comprising administering to a mammal the dietary supplement of claim 11.

* * * * *